(12) United States Patent
Bass (10) Patent No.: US 9,636,097 B2
(45) Date of Patent: May 2, 2017

(54) SURGICAL RETRACTOR WITH A LOCKING RETRACTOR BLADE

(71) Applicant: Tedan Surgical Innovations, LLC., Sugarland, TX (US)

(72) Inventor: Daniel Bass, Half Moon Bay, CA (US)

(73) Assignee: TEDAN SURGICAL INNOVATIONS, LLC., Sugarland, TX (US)

( * ) Notice: Subject to any disclaimer, the term of this patent is extended or adjusted under 35 U.S.C. 154(b) by 365 days.

(21) Appl. No.: 14/447,924

(22) Filed: Jul. 31, 2014

(65) Prior Publication Data

US 2016/0030030 A1 Feb. 4, 2016

(51) Int. Cl.
*A61B 1/32* (2006.01)
*A61B 17/02* (2006.01)

(52) U.S. Cl.
CPC ............... *A61B 17/0206* (2013.01)

(58) Field of Classification Search
CPC .. A61B 17/02; A61B 17/0206; A61B 17/0293
USPC .................................. 606/200–248
See application file for complete search history.

(56) References Cited

U.S. PATENT DOCUMENTS

| | | | |
|---|---|---|---|
| 1,607,788 A | 11/1926 | Atkinson | |
| 3,119,594 A | 1/1964 | Heggem | |
| 3,737,142 A | 6/1973 | Boswell et al. | |
| 4,976,403 A | 12/1990 | Bramblet | |
| 5,902,233 A | 5/1999 | Farley et al. | |
| 7,182,729 B2 | 2/2007 | Abdelgany et al. | |
| 7,758,501 B2 * | 7/2010 | Frasier | A61B 17/02 600/231 |
| 7,850,608 B2 | 12/2010 | Hamada | |
| 7,887,482 B2 | 2/2011 | Hamada | |
| 7,922,658 B2 | 4/2011 | Cohen et al. | |
| 7,931,589 B2 | 4/2011 | Cohen et al. | |
| 7,935,054 B2 | 5/2011 | Hamada | |
| 7,946,982 B2 | 5/2011 | Hamada | |
| 7,988,625 B2 | 8/2011 | Abdelgany et al. | |
| 8,257,255 B2 | 9/2012 | Farley et al. | |
| 8,298,139 B2 | 10/2012 | Hamada | |
| 8,303,499 B2 | 11/2012 | Hamada | |
| 8,357,184 B2 | 1/2013 | Woolley et al. | |

(Continued)

*Primary Examiner* — Matthew Lawson
(74) *Attorney, Agent, or Firm* — Kramer Amado P.C.

(57) ABSTRACT

A surgical retractor includes a retractor body and a retractor arm. The retractor arm includes a first portion configured to operatively connect to the retractor body, and a control assembly configured to control movement of a retractor blade. The control assembly includes a base member having a first opening and a second opening, and movable between a first position and second position. The retractor arm further includes a regulating member to control rotation of the base member and move through the first opening of the base member, a connecting member cooperatively connected to the regulating member, and a barrel member in operative slidable engagement with the second opening formed in the base member. Rotation of the regulating member in a selected direction moves a stem of the regulating member through the first opening thereby forcing the barrel member to slide along the second opening and the base member to pivot relative to the retractor arm between a first position and second position, thereby rotating a connected retractor blade.

15 Claims, 4 Drawing Sheets

(56) References Cited

U.S. PATENT DOCUMENTS

| | | |
|---|---|---|
| 8,360,971 B2 | 1/2013 | Farley et al. |
| 8,435,269 B2 | 5/2013 | Woolley et al. |
| 8,535,320 B2 | 9/2013 | Woolley et al. |
| 8,636,656 B2 | 1/2014 | Nichter et al. |
| 8,727,975 B1 * | 5/2014 | Pfabe ................ A61B 17/0206 600/231 |
| 2004/0193018 A1 * | 9/2004 | Thalgott ................ A61B 17/02 600/227 |
| 2007/0038033 A1 * | 2/2007 | Jones ................ A61B 17/0293 600/219 |
| 2007/0208228 A1 * | 9/2007 | Pavento ............. A61B 17/0293 600/233 |
| 2011/0301422 A1 | 12/2011 | Woolley et al. |
| 2014/0018633 A1 | 1/2014 | Woolley et al. |
| 2014/0114137 A1 | 4/2014 | Reglos et al. |

* cited by examiner

SURGICAL RETRACTOR WITH A LOCKING RETRACTOR BLADE

TECHNICAL FIELD

The invention relates to a surgical retractor, and more particularly relates to a surgical retractor having a control assembly configured for facilitating reciprocating movement, as well as locking a retractor blade in a selected position.

BACKGROUND

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat and may have end prongs of various configurations to make it easier to pull back tissue. The retractor blades may be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

The retractors in use today retract the opening created in the body of the patient in a uniform manner. If the surgeon needs a large opening near the spine, for instance, the opening in the body of the patient must be retracted in a uniform manner. This creates significant trauma for the patient and increases the patient's recovery time.

SUMMARY

In light of the present need for a surgical retractor with a locking retractor assembly, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

The surgical retractor comprises a retractor body, a retractor arm including a first portion configured to operatively connect to the retractor body, and a control assembly configured to control movement of a retractor blade. The control assembly includes a base member having a first opening and a second opening. The control assembly is movable between a first position and second position. The control assembly further includes a regulating member configured to control rotation of the base member and move through the first opening of the base member, a connecting member cooperatively connected to the regulating member, and a barrel member in operative slidable engagement with the second opening formed in the base member.

Rotation of the regulating member in a selected direction moves a stem of the regulating member through the first opening thereby forcing the barrel member to slide along the second opening and the base member to pivot relative to the retractor arm between a first position and second position.

In an embodiment of the surgical retractor, the base member includes a first portion configured to engage the third retractor blade and a second portion configured to engage the retractor arm.

In another embodiment of surgical retractor, the second opening of the base member is formed therein. The second opening is configured to facilitate slidable movement of the barrel member between a first position and a second position within the second opening.

In another embodiment of the surgical retractor the regulating member includes a stem configured to slide through the first opening formed in the base member. The regulating member and connecting member are threadably engaged such that rotation of the regulating member forces the stem of the regulating member to move perpendicularly relative to the axis of the retractor arm, through the first opening, from a first position to a second position. The second portion of the base member has an aperture formed therein to receive the third retractor blade.

In another embodiment, the retractor arm is a third retractor arm, and the surgical retractor further includes a first retractor arm and a second retractor arm connected to the retractor body. The first retractor arm and second retractor arm are configured to rotate in opposing directions. The third retractor arm is positioned intermediate to the first retractor arm and the second retractor arm along the retractor body. As such, the third retractor arm is configured to rotate the retractor blade in response to movement of the regulating member in a direction perpendicular to the axis of the third retractor arm. Slidable movement of the base member forces the base member to rotate relative to the retractor arm. The regulating member in combination with the connecting member forces the stem to move between a first position and a second position within the base member, and further forces the barrel member within the slot to move from a first position to a second position within the base member, thereby rotating the base member and the third retractor blade.

In an embodiment of the retractor, the surgical retractor includes a connecting pin rotatably connects the retractor arm to the base member. The base member has an aperture formed therein to receive the connecting pin to rotatably connect the first portion of the base member to the retractor arm. The connecting pin extends through an opening formed in the base member and an opening formed in the retractor arm permitting the base member to pivot relative to the retractor arm. The regulating member is a fastener having a series of internal threads configured to operatively engage the connecting member having external threads. The barrel member has an opening formed therein configured to receive the connecting member therethrough. The barrel includes dual slidable members formed on opposing sides of the barrel member. The dual slidable members have a generally cylindrical shape facilitating slidable movement within the second opening of the base member.

According to an embodiment, a surgical retractor includes a retractor body and a retractor arm. The retractor arm includes a first portion and a second portion. The first portion is attached to the retractor body and the second portion is rotatably attached to the first portion. The second portion is configured to retain a retractor blade and to rotate about an axis parallel to a line drawn along a length of the retractor arm.

BRIEF DESCRIPTION OF THE DRAWINGS

Examples of the invention are illustrated, without limitation, in the accompanying figures in which like numeral references refer to like elements and wherein.

To facilitate understanding, identical reference numerals have been used to designate elements having substantially the same or similar structure and/or substantially the same or similar function

DETAILED DESCRIPTION

For simplicity and illustrative purposes, the principles are shown by way of examples of systems and methods described. In the following description, numerous specific details are set forth in order to provide a thorough understanding of the examples. It will be apparent however, to one of ordinary skill in the art, that the examples may be practiced without limitation to these specific details. In other instances, well known methods and structures are not described in detail so as not to unnecessarily obscure understanding of the examples.

One common problem with conventional retractors and the connected retractor blades, are that when the retractor blades are extended from the retractor body, the retractor blades move relatively "freely" when engaged with a body member and do not lock into a selected position. This can be problematic, as most surgical procedures require the surgeon to perform with detail and precision. As such, retractor blades that move freely while a surgeon is attempting to perform a procedure can be distracting, and potentially cause the doctor to make a mistake while performing a procedure on a patient.

The foregoing advantages of the invention are improvements of those that can be achieved by the various exemplary embodiments and are not intended to be exhaustive or limiting of the possible advantages which can be realized. Thus, these and other advantages of the various exemplary embodiments will be apparent from the description herein or can be learned from practicing the various exemplary embodiments, both as embodied herein or as modified in view of any variation that may be apparent to those skilled in the art. Accordingly, the invention resides in the novel methods, arrangements, combinations, and improvements herein shown and described in various exemplary embodiments.

Retractors generally provide retractor arms that are adjustable. The retractor arms extend generally outward from the retractor body and may be configured to rotate and/or move in several different directions. As such, it is common that the retractor arms may move relatively freely until they are inserted and adjusted to apply force to the body member(s). The unpredictable movement and/or "play" of the retractor arms can be a distracting to the user during a surgical procedure. Accordingly, it is desirable to provide a surgical retractor including a lockable retractor assembly with one or more retractor arms that may be locked in a selected position, eliminating unnecessary movement of the retractor arms during usage and providing the doctor controlled precision during use of the retractor.

Figure 1:
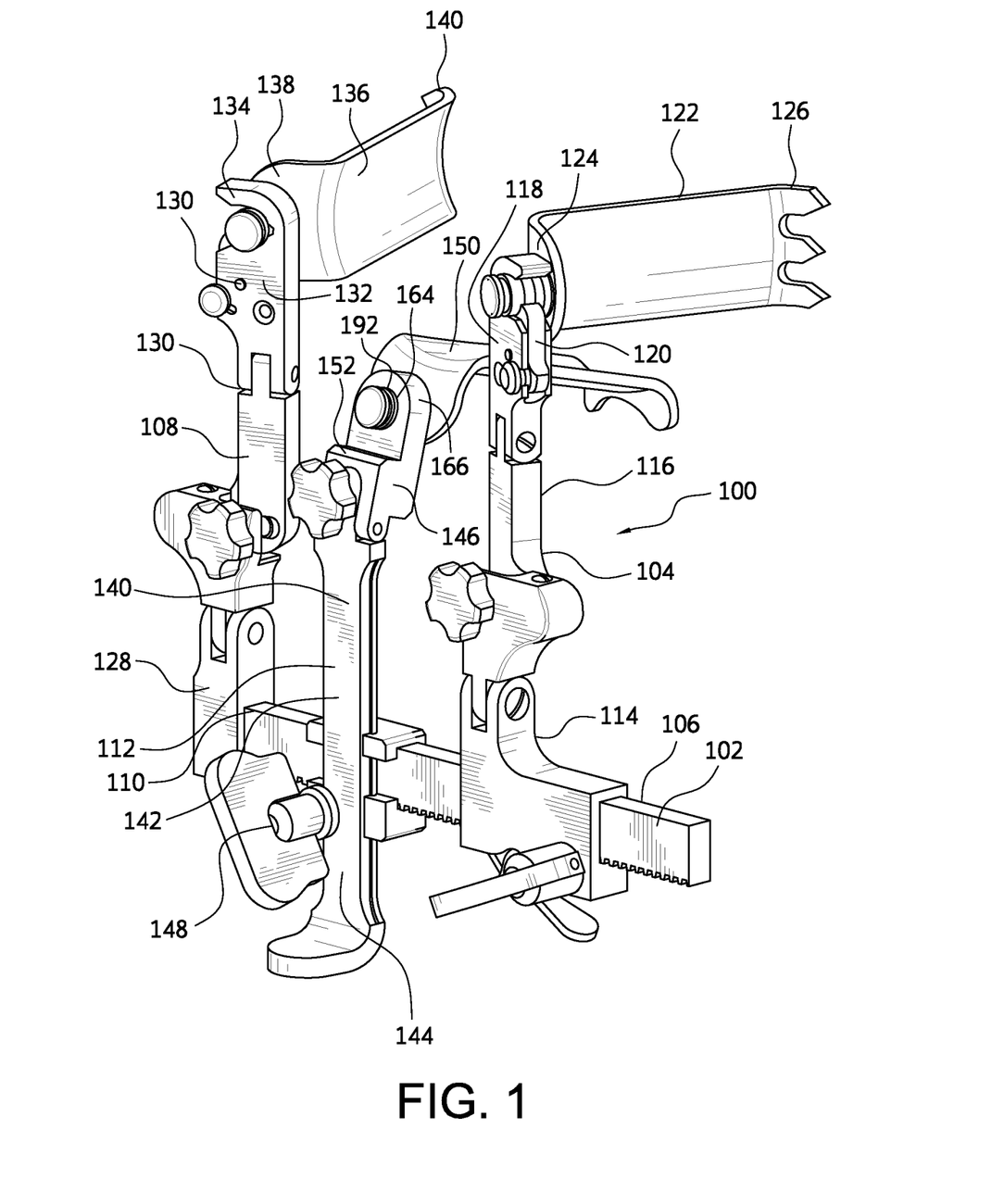
FIG. 1 shows a perspective diagram of an exemplary surgical retractor with rotating blades and a locking third retractor assembly, in accordance with the present invention.

Referring now to the drawings, wherein the illustrations are for purposes of describing one or more embodiments and not for the purposes of limiting the same, FIG. 1 illustrates an embodiment of the surgical retractor generally designated by the reference numeral 100. The surgical retractor 100 includes a retractor body 102, a first retractor arm 104 operatively connected to the retractor body 102 at a first end 106 of the retractor body 102, a second retractor arm 108 operatively connected to a second end 110 of the retractor body 102, and a retractor arm 112, which may be referred to as a third retractor arm 112, operatively connected to the retractor body 102, generally intermediate to the first retractor arm 104 and second retractor arm 108. The first retractor arm 104 generally includes a first portion 114 and a second portion 116. The first retractor arm 104 is connected to the retractor body 102 by the first portion 114. The second portion 116 of the first retractor arm 104 is operatively connected to the first portion 114, and includes at a distal end 118 having a connector 120. The connector 120 is configured to receive a retractor blade 122. Notably, it is contemplated that the connector 120 may be configured for use in a variety of manners. One example of a connector 120 or use with a surgical retractor blade 122 is described in U.S. Pat. No. 7,537,565 by Daniel Bass and entitled "Surgical Retractor with Rotating Blades". This application is hereby incorporated by reference for all purposes in its entirety.

The retractor blade 122 includes a proximal end 124 provided generally proximate to the connector 120 and a distal end 126 which is configured for insertion into the body of a patient. The second portion 116, which retains the retractor blade 122 may rotate generally around an axis parallel to a line drawn along a length of the retractor arm 104. This rotation may cause the distal end 126 of the retractor blade 122 to tilt or angle thus exposing a larger area inside the body of a patient without significantly increasing an insertion point. Because the distal end 118 of the retractor blade 122 moves through a larger range of motion than the proximal end 114, the insertion point may be smaller than the area inside the body of the patient.

The second retractor arm 108 includes a first portion 128 connecting the second retractor arm 108 and a second portion 130 connected to the retractor body 102 by the first portion 128. Similar to that the first retractor arm 104, the second portion 130 of the second retractor arm 108 may be rotatably attached to the first portion 128 and may include at a distal end 132 including a connector 134 for receiving a second retractor blade 136. The second retractor blade 136 may include a proximal end 138 near the connector 134 and a distal end 140 which may also be inserted into the body of a patient. Similar to the first retractor arm 104, the second portion 130 of the second retractor arm 108 receives the second retractor blade 136 may rotate around an axis parallel to a line drawn along a length of the retractor arm 108. This rotation causes the distal end 140 of the retractor blade 136 to tilt or angle thus exposing a larger area inside the body of a patient without significantly increasing an insertion point. Because the distal end 140 of the retractor blade 136 moves through a larger range of motion than the proximal end 138, the insertion point may be smaller than the area inside the body of the patient.

When the retractor blades 122 and 136 are inserted into the body of a patient, the second portions 116 and 130 of the respective first retractor arm 104 and second retractor arm 108 may be rotated. This forces the respective distal ends 126 and 140 to separate and expose a larger area inside the body of the patient than the area of the insertion point. The proximal ends 124 and 138 of the retractor blades 122 and 136 may lie near the insertion point but may not significantly increase the insertion area as the proximal ends 124 and 138 move through a smaller range of motion than the distal ends 126 and 140 of the retractor blades 122 and 136.

The retractor arm 112 generally includes a first portion 142 connected to the retractor body 102, a second or lower portion 144, and a third portion 140 connected to a retractor blade 150, which may be referred to as a third retractor blade 150. The third retractor blade 150 is operatively connected to a connector 146 which also may be a control assembly 146 configured to control rotational movement of the retractor arm 112. As shown, the first portion 142 of the retractor arm 112 is adjustably connected to the retractor body 102 and may be raised and lowered relative to the retractor body 102 via a clamping member 148.

As shown, the lower portion 144 of the retractor arm 112 is insertable in the clamping member 148, thereby permitting movement of the retractor arm 112 to be raised and/or lowered relative to the body 102. The retractor arm 112 further includes a retractor blade 150, which may be connected to the control assembly 146 at an aperture 192 formed in the retractor 112. As such, reciprocating movement of the retractor blade 150 may be controlled by adjusting the control assembly 146. Notably, it is contemplated that the control assembly 146 may be provided in combination with the first retractor arm 104 and/or second retractor arm 108, to control rotational movement of the respective retractor blades 122 and 136. As shown, the third retractor arm 112 may be positioned on the retractor body 102 generally intermediate to the first retractor arm 104 and second retractor arm 108.

Figure 2A:
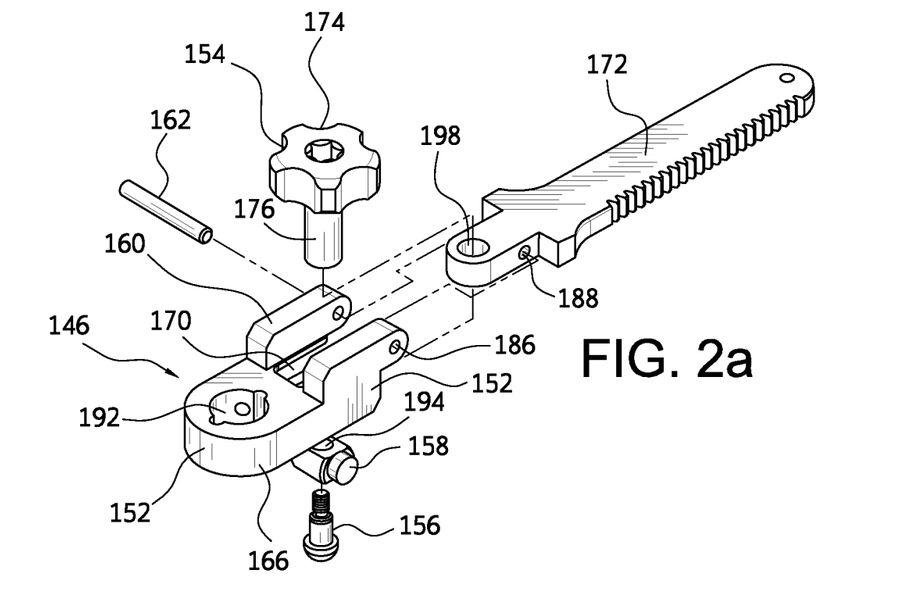
FIG. 2a shows an exploded top perspective view of the locking third retractor assembly of FIG. 1, illustrating a third retractor body connection to a base member.
Figure 2B:
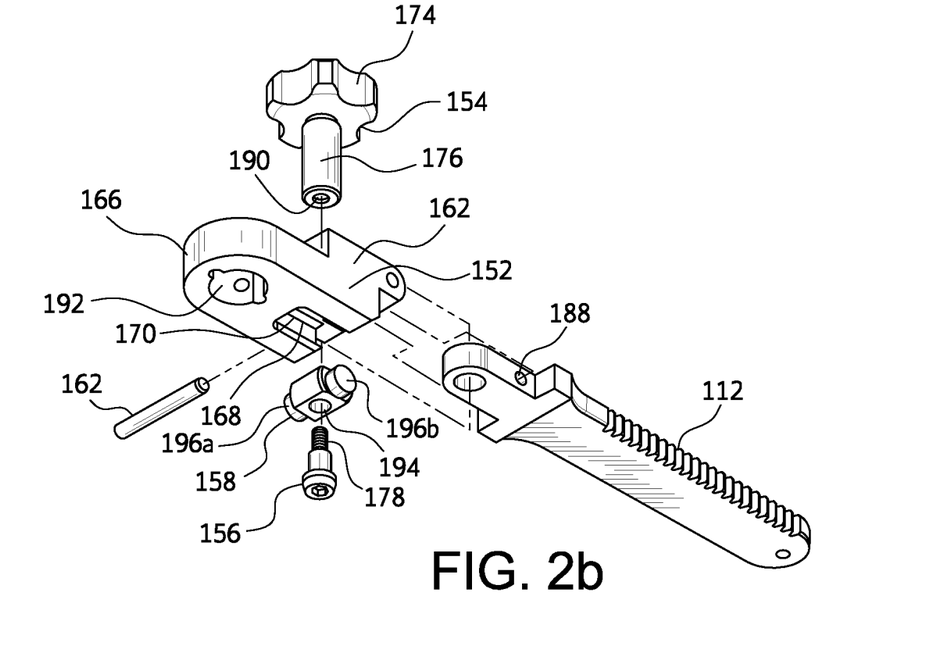
FIG. 2b shows an exploded bottom perspective view of the locking third retractor assembly of FIG. 1, illustrating a barrel operative relationship with a base member.

Continuing now to FIGS. 2a and 2b, there an exploded illustration of the retractor arm 112 and control assembly 146 are shown. The control assembly 146 is configured to facilitate locking controlled movement of the third retractor blade 150, permitting a user to rotate and subsequently lock the retractor blade 150 into a selected position. As shown, the control assembly 146 includes a base member 152 having a first portion 160 configured for connection to the third retractor blade 150 and a second portion 166, configured to receive the retractor arm 112.

In addition to the base member 152, the control assembly 146 further includes a regulating member 154 adapted to control the reciprocating rotational movement the base member 152 in conjunction with the connected retractor blade 150. The base member 152 further includes a connecting member 156 or fastener, configured to cooperatively engage the regulating member 154, a connecting pin 162 insertable through an opening 188 formed in the third retractor arm 112 and an opening 186 formed in the base member 152, respectively. As such, the combination of the connecting pin 162, a reciprocating base member 152 and regulating member 154 provide a pivotal connection therebetween. The control assembly 146 further includes a barrel member 158 configured to be slidably positioned within the base member 152 and provided generally intermediate to the regulating member 154 and connecting member 156.

As shown in FIGS. 1, 2a and 2b the base member 152 includes a second portion 166 having an second opening or aperture 192 formed therein configured to receive an extension 164 of the third retractor blade 150, and a first portion 160 configured to receive a portion of the retractor arm 112. As shown, the aperture 192 of the base member 152 facilitates connection between the threaded extension 164 of the retractor blade 150 and the base member 152.

As shown in FIGS. 2a and 2b, the second portion 166 includes a second opening or slot 168 formed generally laterally therein, and configured to receive the barrel member 158. The second opening 168 or slot is dimensioned to facilitate slidable movement of the barrel member 158, between a first position and a second position, which facilitates rotational movement of the retractor arm 108. The base member 152 further includes a first opening 170, extending generally through the first portion 160 and second portion 166 of the base member 152 formed therein to receive a stem 176 or sleeve of the regulating member 154.

Figure 3:
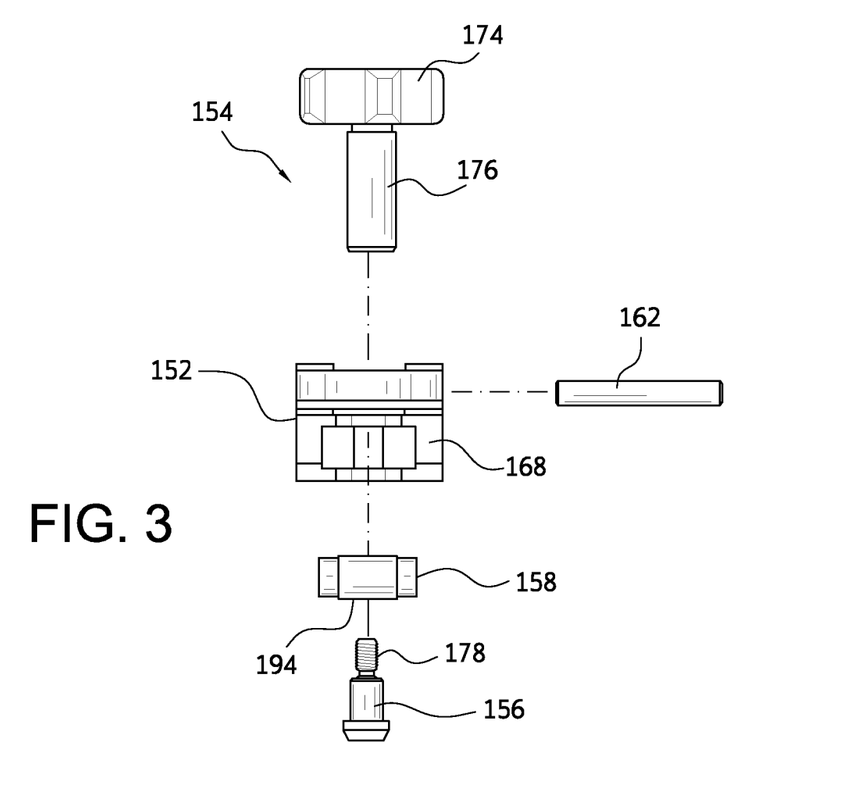
FIG. 3 is an exploded frontal view of the base member.
Figure 4:
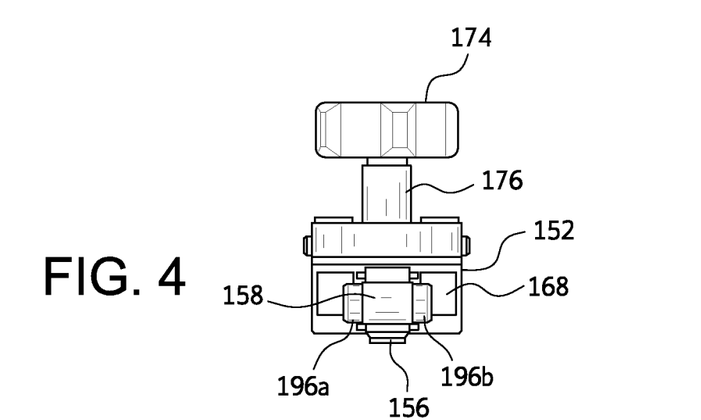
FIG. 4 is a frontal view of the base member of the third retractor assembly.

The barrel member 158 further includes a dual sliding members 196a and 196b having a generally cylindrical configuration to facilitate slidable movement about the second opening 168. As shown in FIGS. 3 and 4, the barrel member 158 has an aperture 194 formed therein, configured to receive the connecting member 156 therethrough As shown, the sliding members 196a-b extend from the body of the barrel member 158 in generally opposing directions to provide controlled sliding movement within.

The stem 176 of the regulating member 154 extends generally outward from the knob 174 and is configured to slide through the first opening 170 of the base member and an opening 198 formed in the retractor arm 112. As such the stem 176 operatively engages the connecting member 156 fastener. As shown, knob 174 is formed generally at the distal end of the regulating member 154, facilitating manual adjustment by a user with his/her hands. As shown in FIG. 2b, the stem 176 includes an opening 190 formed generally at the end of the stem and extending generally therein and configured to receivably engage the connecting member 156. The opening 190 may include inner threads to receive the connecting member 156. As shown in FIG. 3, the connecting member 156 including a series of outer threads 178, configured to cooperatively engage inner threads provided in the opening 190 of the stem 176.

The connecting member 156 extends through the barrel member 158 into the opening 190 formed in the stem 176. Accordingly, the regulating member 154 and connecting member member 156 are threadably engaged, such that rotation of the regulating member 154 forces the connecting member 156 to move towards or away from the stem 176 through the opening 190, thereby forcing the stem 176 of the regulating member 154 to move laterally through the opening 170 between a first position to a second position. In operation, the third retractor arm 150 may be moved between a first position and second position and locked in a selected position.

Figure 5:
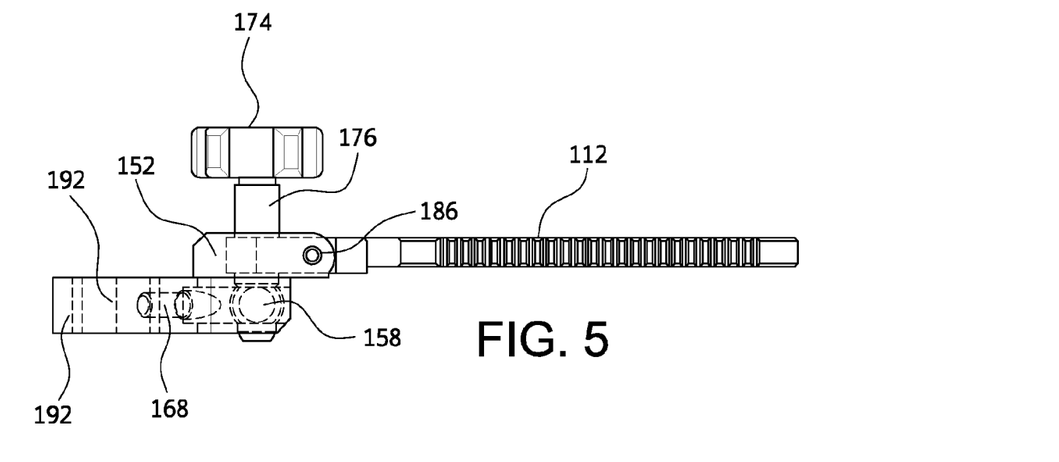
FIG. 5 is a side view of the locking retractor assembly illustrating the retractor assembly in a first position.
Figure 6:
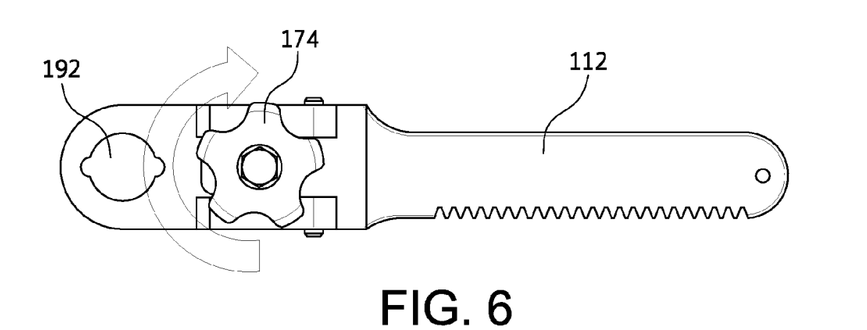
FIG. 6 is a top plan view of the third locking retractor assembly illustrating the retractor assembly in a first position.

As shown in FIG. 5, in a first position, the regulating member 154 and stem 176 are in a generally open extended position, extending away from the arm 112. As shown in FIG. 6, rotation of the regulating member 154 and threaded engagement with the connecting member 156 forces the regulating member 154 and stem 176 to move through the opening 170 as the regulating member 154 is rotated. The regulating member 154 and stem 176 move in a direction generally perpendicular relative to the axis of the third retractor arm 112, through the first opening, from a first position to a second position As the connecting member 156 is drawn through the opening 170 movement of the stem 176 forces the barrel member 158 to slide along the second opening 168.

Figure 7:
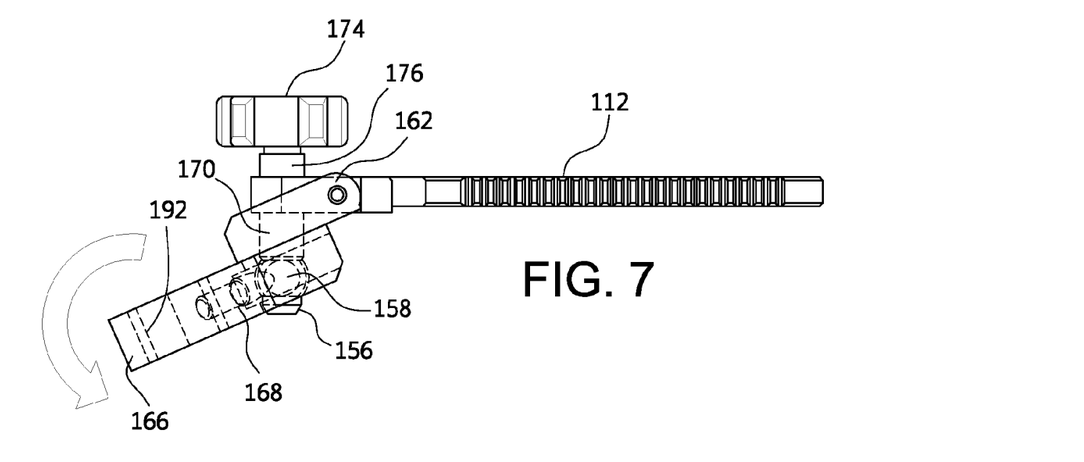
FIG. 7 is a side view of the locking retractor assembly illustrating the retractor assembly in a second position.

As shown the connecting pin 162 is inserted through an opening 188 formed in the retractor arm 112 and an opening 186 formed in the base member 152. Movement of the barrel member 158 along the opening 168 provides a force, biasing the base member 152 to pivot about the connecting pin 162 in a first direction. As shown in FIG. 7, as the base member 152 pivots or rotates, the second portion 166 of the base member 152 forces the retractor blade to rotate as shown in FIG. 7. Movement of the stem 176 of the regulating member 154 through the base member 152 between a first position to a second position forces the barrel member 158 to slide along the slot 168 from a first position to a second position thereby rotating the base member 152 and connected third retractor blade. As such, the forces applied by the stem 176 in cooperation with the connecting pin 162 lock the retractor blade 150 in a selected position.

Conversely, rotation of the regulating member 154 in an opposing direction causes the connecting member 156 to retreat from the stem 176 and forces the base member 152 to pivot about the connecting pin 162 in a second direction. As such, the retractor blade 150 is moved towards the retractor arm 112

What has been described and illustrated herein are examples of the systems and methods described herein along with some of their variations. The terms, descriptions and figures used herein are set forth by way of illustration only and are not meant as limitations. Those skilled in the art will recognize that many variations are possible within the spirit and scope of these examples, which are intended to be defined by the following claims and their equivalents in which all terms are meant in their broadest reasonable sense unless otherwise indicated.

What is claimed is:

1. A surgical retractor comprising:
   a retractor body; and
   a retractor arm including a first portion configured to operatively connect to the retractor body, a control assembly configured to control movement of a retractor blade, the control assembly including a base member having a first opening and a second opening and movable between a first position and second position, a regulating member configured to control rotation of the base member and move through the first opening of the base member, the regulating member including a stem, a connecting member cooperatively connected to the regulating member, and a barrel member in operative slidable engagement with the second opening formed in the base member,
   wherein rotation of the regulating member in a selected direction moves the stem of the regulating member through the first opening thereby forcing the barrel member to slide along the second opening and the base member to pivot relative to the retractor arm between a first position and second position.

2. The surgical retractor of claim 1, wherein the base member includes a first portion configured to engage the retractor arm and a second portion configured to engage the retractor blade.

3. The surgical retractor of claim 1, wherein the second opening of the base member is formed therein, and the second opening is configured to facilitate slidable movement of the barrel member between a first position and a second position within the second opening.

4. The surgical retractor of claim 1, wherein the regulating member and connecting member are threadably engaged such that rotation of the regulating member forces the stem of the regulating member to move perpendicularly relative to the axis of the retractor arm, through the first opening, from a first position to a second position.

5. The surgical retractor of claim 2, wherein the second portion of the base member has an aperture formed therein to receive the retractor blade.

6. The surgical retractor of claim 1, wherein in the retractor arm is a third retractor arm, and the surgical retractor further includes a first retractor arm and a second retractor arm connected to the retractor body and configured to rotate in opposing directions, wherein the third retractor arm is positioned intermediate to the first retractor arm and the second retractor arm, the third retractor arm is configured to rotate the retractor blade in response to movement of the regulating member in a direction perpendicular to the axis of the third retractor arm.

7. The surgical retractor of claim 6, wherein slidable movement of the base member forces the base member to rotate relative to the retractor arm.

8. The surgical retractor of claim 6, wherein the rotation of the regulating member in combination with the connecting member forces the stem to move between a first position and a second position within the base member, and further forces the barrel member within the second opening to move from a first position to a second position within the base member, thereby rotating the base member and the third retractor blade.

9. The surgical retractor of claim 1, wherein a connecting pin rotatably connects the retractor arm to the base member.

10. The surgical retractor of claim 9, wherein the base member has an aperture formed therein to receive the connecting pin to rotatably connect the first portion of the base member to the retractor arm.

11. The surgical retractor of claim 10, wherein the connecting pin extends through an opening formed in the base member and an opening formed in the retractor arm such that the base member pivots relative to the retractor arm.

12. The surgical retractor of claim 1, wherein the regulating member is a fastener having a series of internal threads configured to operatively engage the connecting member having external threads.

13. The surgical retractor of claim 1, wherein the barrel member has an opening formed therein configured to receive the connecting member therethrough.

14. The surgical retractor of claim 13, wherein the barrel includes dual slidable members formed on opposing sides of the barrel member.

15. The surgical retractor of claim 14, wherein the dual slidable members have a generally cylindrical shape facilitating slidable movement within the second opening of the base member.

* * * * *